US008389773B2

(12) United States Patent
Parton et al.

(10) Patent No.: US 8,389,773 B2
(45) Date of Patent: Mar. 5, 2013

(54) CYCLOHEXANONE PRODUCTION PROCESS WITH IMPURITIES REMOVAL (75) Inventors: Rudy Francois Maria Jozef Parton, Winkelse (BE); Johan Thomas Tinge, Sittard (NL)

(73) Assignee: DSM IP Assets B.V., Heerlen (NL)

( * ) Notice: Subject to any disclaimer, the term of this patent is extended or adjusted under 35 U.S.C. 154(b) by 203 days.

(21) Appl. No.: 12/808,815

(22) PCT Filed: Dec. 16, 2008

(86) PCT No.: PCT/EP2008/067629
§ 371 (c)(1),
(2), (4) Date: Oct. 12, 2010

(87) PCT Pub. No.: WO2009/080618
PCT Pub. Date: Jul. 2, 2009

(65) Prior Publication Data
US 2011/0028763 A1     Feb. 3, 2011

(30) Foreign Application Priority Data
Dec. 20, 2007   (EP) .................................. 07024766

(51) Int. Cl.
*C07C 45/82* (2006.01)
*B01J 8/00* (2006.01)
(52) U.S. Cl. ...................... 568/350; 422/610
(58) Field of Classification Search .............. 568/350; 422/610
See application file for complete search history.

(56) References Cited

U.S. PATENT DOCUMENTS

| 3,305,586 A | 2/1967 | Bernard |
| 4,272,326 A | 6/1981 | Hertzog et al. |
| 4,306,944 A | 12/1981 | Murthy et al. |

FOREIGN PATENT DOCUMENTS

EP   0 450 498   10/1991

OTHER PUBLICATIONS

International Search Report for PCT/EP2008/067629, mailed Apr. 23, 2009.
Written Opinion of the International Searching Authority for PCT/EP2008/067629, mailed Apr. 23, 2009.
M.T. Musser: "Ullmann's Encyclopedia of Industrial Chemistry: Cyclohexanol and Cyclohexanone", 2005, Wiley-VCH, Weinheim, XP002482245.

*Primary Examiner* — Sikarl Witherspoon
(74) *Attorney, Agent, or Firm* — Nixon & Vanderhye P.C.

(57) ABSTRACT

The present invention relates to a method for preparing cyclohexanone from phenol in a first process, the first process being a cyclohexanone production process comprising hydrogenating phenol to form a product stream comprising cyclohexanone, phenol and side-products (RSP), including cyclohexanol and undesirable side-product; separating at least part of the product stream having a lower boiling point than cyclohexanone have been removed, into a first fraction comprising cyclohexanone and a second fraction comprising phenol, cyclohexanol and RSP, using distillation; and separating the second fraction into a third fraction, rich in cyclohexanol and comprising RSP, and a fourth fraction, rich in phenol and comprising RSP, using distillation. The invention further relates to an installation for carrying out a method of the invention.

10 Claims, 8 Drawing Sheets

CYCLOHEXANONE PRODUCTION PROCESS WITH IMPURITIES REMOVAL

This application is the U.S. national phase of International Application No. PCT/EP2008/067629, filed 16 Dec. 2008, which designated the U.S. and claims priority to European Application No. 07024766.3, filed 20 Dec. 2007, the entire contents of each of which are hereby incorporated by reference.

The invention relates to a method for the preparation of cyclohexanone from phenol and to a plant suitable for carrying out a method according to the invention.

Cyclohexanone can be employed as an industrial solvent or as an activator in oxidation reactions. It can also be used as an intermediate, inter alia in the production of adipic acid, cyclohexanone resins, caprolactam, nylon 6 or nylon 6,6.

Cyclohexanone is conventionally prepared from phenol by catalytic hydrogenation in a phenol hydrogenation reactor, e.g. using a platinum or a palladium catalyst. The reaction can be carried out in the liquid phase or the vapour phase. [Kirk-Othmer Encyclopedia of Chemical Technology, e.g. 3.sup.rd Edition, Vol 7 (1979) p. 410-416; I. Dodgson et al. "A low Cost Phenol to Cyclohexanone Process", Chemistry & Industry, 18, Dec. 1989, p 830-833; or M. T. Musser "Cyclohexanol and Cyclohexanone", Ullmann's Encyclopedia of Industrial Chemistry (7.sup.th Edition, 2007), (hereafter "Musser")].

In the preparation of cyclohexanone from phenol, typically cyclohexanol (which can be considered an intermediate product useful for further conversion to cyclohexanone) and various undesirable side-products are formed.

The cyclohexanone is typically recovered by a distillation process as a product rich in cyclohexanone (usually ≧90 wt. %) or as an essentially pure product (≧99 wt. %). In distillation, a fluid is separated into at least two fractions. When comparing two fractions, one may be called a "light" fraction, the other a "heavy" fraction. In particular when reference is made herein to a "light" fraction or a "heavy" fraction in relation to a separation by distillation, these terms are used herein relative to each other in a specific distillation step, to distinguished the fraction with the lower boiling point (the light fraction) from the fraction with the higher boiling point (the heavy fraction). Thus, a specific compound can be a "heavy" compound (mainly found in the heavy fraction) in a first distillation step, and a "light" compound (mainly found in the light fraction) in a second distillation step. As generally known, separation of a mixture into a heavy fraction and a light fraction is never absolute.

Figure 1:
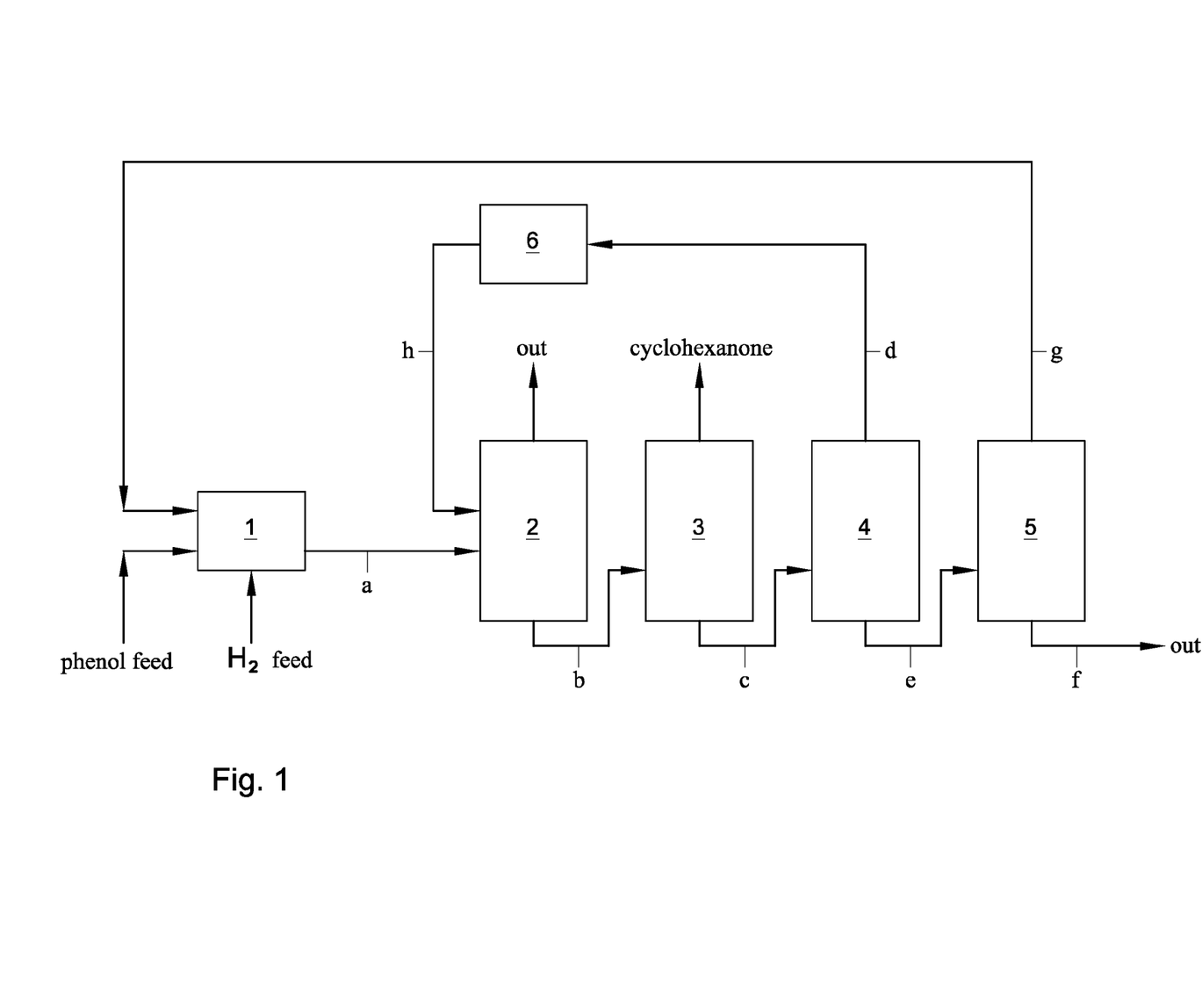
FIG. 1 schematically shows a conventional installation for preparing cyclohexanone from phenol feedstock.

A conventional process for the preparation and recovery of cyclohexanone from phenol feedstock is schematically shown in FIG. 1.

Cyclohexanone is prepared in hydrogenation reaction section (1).

The reaction section in particular comprises a hydrogenation reaction section (which during use is supplied with hydrogen and phenol) and may comprise additional equipment. For instance if hydrogenation is to take place in a vapour phase: upstream of section (1) an evaporator and/or downstream of section (1) a condenser, may be arranged, e.g. as shown in Musser (FIG. 1 thereof) or in U.S. Pat. No. 3,305,586.

Cyclohexanone, (unreacted) phenol and side-product, such as cyclohexanol is usually recovered from the stream leaving the reaction section using a number of distillation sections. A distillation section, as used herein is an installation comprising one distillation column or a plurality of distillation columns in parallel, each having the same functionality. Further the section may comprise other components typical of a distillation unit.

In an optional first distillation section (2) (the pre-distillation section, i.e. a first part of a distillation section upstream of a distillation section wherein cyclohexanone is recovered) light components, e.g. benzene, cyclohexane, water are removed from the reaction product, which reaction product enters the distillation section (2) via conduit a and h, whereas cyclohexanone, residual phenol, cyclohexanol and other side-products leave the pre-distillation section as a bottom fraction via conduit b.

This bottom fraction is distilled in a second distillation section (3) (the main distillation section, i.e. wherein cyclohexanone is recovered). Herein cyclohexanone is recovered from the process stream as a light fraction. This heavy fraction of distillation section (3) contains residual phenol, cyclohexanol, various side-products, and in general still some cyclohexanone. This heavy fraction leaves the distillation section (3) via conduit c. Suitable distillation conditions are known in the art, see e.g. U.S. Pat. No. 2,829,166 or U.S. Pat. No. 3,076,810. From the heavy fraction, typically the valuable components residual phenol, cyclohexanol and cyclohexanone are recovered.

Cyclohexanol is typically recovered from this heavy fraction leaving the main distillation as a light fraction in a (first) post-distillation section (4) (post-distillation meaning downstream of the main distillation wherein cyclohexanone is recovered). This light fraction, which also contains some cyclohexanone, is a cyclohexanol-rich stream, usually comprising at least 70 wt. % cyclohexanol, in particular at least 80 wt. % cyclohexanol. This light fraction is subsequently led to a cyclohexanol dehydrogenation section (6) via conduit d (see e.g. Musser, paragraph 3.5). In cyclohexanol dehydrogenation section (6) cyclohexanol is partially dehydrogenated to form cyclohexanone. Typically, section (6) comprises a dehydrogenation reactor, and usually further an evaporator for evaporating the feed upstream of the reactor, and a condenser for condensing the product stream leaving the reaction. The cyclohexanone-enriched stream leaving section (6) is then led to pre-distillation section (2), via conduit h.

Phenol forms part of the bottom fraction of the first post-distillation. This bottom fraction is fed to a further post-distillation section (5), via conduit e, wherein remaining valuable components, mainly phenol and in general some cyclohexanone and some cyclohexanol, are recovered as the light fraction and returned to the phenol hydrogenation section, via conduit g. The bottom fraction from the last post-distillation is typically discarded via conduit f, e.g. incinerated or used for steam generation in a boiler house. Alternatively, the bottom fraction may be used as a low-cost material for a residual product, e.g. tar, asphalt, shoe polish or the like.

The inventors have realised that in the above described process, the energy consumption (for a given cyclohexanone production capacity) of the plant increases in time. Also, they found that the separation efficiency in the distillation sections decreases in time. Thus, capacity decreases and production cost increases in time. The distillation section(s) may even become a bottleneck for the capacity of the cyclohexanone plant.

In particular, the inventors found that energy consumption can be reduced and separation efficiency can be increased by draining a part of the bottom fraction of the main distillation, and/or by additional draining of any fraction of a post-distillation section. The drained fraction is usually discarded. However, draining is undesired for various reasons. With the drained fraction, useful product (cyclohexanone and/or cyclohexanol and/or phenol, the latter two being precursors for cyclohexanone) is wasted. Further, the drained fraction may impose a burden on the environment.

It is an object of the invention to provide a method for preparing cyclohexanone, wherein one or more of the above drawbacks are overcome or at least alleviated.

The inventors have found that it is possible to reduce energy consumption and/or improve production capacity in a process for converting phenol to cyclohexanone by hydrogenation, without having to waste substantial amounts of useful product by rerouting the process stream in a specific way, namely by leading a specific fraction of the product stream, said fraction comprising cyclohexanone and one or more other useful substances other than cyclohexanone and further undesirable side-product to a different production process. The useful substance typically is selected from cyclohexanol and phenol.

The invention is inter alia based on the insight that above mentioned drawbacks exist and are caused by specific undesirable side-products notably dicyclohexyl, which undesirable side-products have been found to accumulate in the conventional cyclohexanone plant based on phenol feedstock, since at least a substantial part of such side-products is present in one or more of the fractions that are typically recycled in the plant.

Such side-products, notably dicyclohexyl, are referred to herein below as "recycling side-product" (RSP) for the tendency of these products to accumulate in a conventional process as schematically shown in FIG. 1. Such side-products may even accumulate to levels of about 10 wt. % or more of one or more streams, before a steady state may be reached. Dicyclohexyl usually forms a major portion of these (recycling) side-products. The terms, "RSP", "further side-products" and "undesirable side-products" are in particular used herein for a side-product, such as dicyclohexyl, having a tendency to accumulate in the cyclohexanone production process, as shown in FIG. 1.

Without being bound by theory, it is contemplated that phenol plays an important role in the accumulation of RSP in a cyclohexanone process with phenol as feedstock, for instance as shown in FIG. 1.

To "accumulate" means that at least initially more of such side-product is formed from the process (in, e.g., the phenol hydrogenation reactor of) than is removed from the process as schematically shown in FIG. 1.

In particular, a product (or product mixture) with a tendency to accumulate may be an undesirable side-product (or mixture of undesirable side-products), formed in a small amount, for instance an amount of less than 1 wt. %, based on the phenol feed, in particular in an amount of less than 0.5 wt. %, based on the phenol feed, but which accumulates in said conventional process as schematically shown in FIG. 1, to a steady state concentration of more than 5 wt. % in a process stream, for instance in stream c and/or e whereby the accumulation causes problems in section (4) and/or section (5), respectively.

The inventors have further realised that it is not necessary to drain the plant at intervals (or continuously) and discard useful substances, such as cyclohexanone, cyclohexanol and phenol, or having to invest in extra recovery facilities to recover one or more of these useful substances, in order to avoid accumulation of RSP, in particular dicyclohexyl, to a level that is detrimental to the process. In particular, the inventors have realised that it is possible to combine the production of cyclohexanone from phenol with another process for preparing a chemical substance of interest, wherein RSP, which would normally accumulate in the cyclohexanone production plant based on phenol feedstock, is conveniently removed from the substance of interest produced in said other process without unacceptable disturbances.

Accordingly, the present invention relates to a method for preparing cyclohexanone from phenol in a first process, the first process being a cyclohexanone production process making use of a catalyst comprising at least one catalytically active metal selected from platinum and palladium, comprising a) hydrogenating phenol to form a product stream comprising cyclohexanone, phenol and side-products, including cyclohexanol and recycling side product (RSP);

b) separating at least part of the product stream, or at least part of the product stream from which one or more components having a lower boiling point than cyclohexanone have been removed, into a first fraction comprising cyclohexanone and a second fraction comprising phenol, cyclohexanol and RSP, using distillation;

c) separating the second fraction into a third fraction, rich in cyclohexanol (preferably comprising at least 70 wt. %, more preferably at least 80 wt. % of cyclohexanol) and comprising RSP, and a fourth fraction, rich in phenol (preferably comprising at least 65 wt. % of phenol) and usually comprising RSP, using distillation; and d) continuously or discontinuously introducing at least part of said third fraction rich in cyclohexanol and comprising RSP into a second process, in which second process RSP is removed from cyclohexanol and/or a conversion product of cyclohexanol formed in the second process.

The third fraction, rich in cyclohexanol, may in particular be a light fraction of the distillation step wherein the third fraction is provided.

Preferably, the introducing into a second process of at least part of the third fraction rich in cyclohexanol and comprising RSP in step c) is done after said at least part has been treated in a dehydrogenation process.

The invention further relates to a method for preparing cyclohexanone from phenol in a first process, the first process being a cyclohexanone production process making use of a catalyst comprising at least one catalytically active metal selected from platinum and palladium, comprising a) hydrogenating phenol to form a product stream comprising cyclohexanone, phenol and side-products, including cyclohexanol and recycling side product (RSP);

b) separating at least part of the product stream, or at least part of the product stream from which one or more components having a lower boiling point than cyclohexanone have been removed, into a first fraction comprising cyclohexanone and a second fraction comprising phenol, cyclohexanol and RSP, using distillation;

c) separating the second fraction into a third fraction, rich in cyclohexanol (preferably comprising at least 70 wt. %, more preferably at least 80 wt. % of cyclohexanol) and usually comprising RSP, and a fourth fraction, rich in phenol (preferably comprising at least 65 wt. % of phenol) and comprising RSP, using distillation; and d) continuously or discontinuously introducing at least part of said fourth fraction rich in phenol and comprising RSP into a second process, in which second process RSP is removed from phenol and/or a conversion product of phenol formed in the second process.

The fourth fraction in this process is usually at least partially subjected to a further fractionation by distillation, whereby a light fraction (the fifth fraction) comprising phenol and RSP is formed, which—according to an embodiment of the invention—is thereafter at least partially introduced into the second process. The small sixth fraction, enriched in heavies, is usually drained. It is to be understood that the phrase "continuously or discontinuously introducing at least part of said fourth fraction rich in phenol and comprising RSP into a second process" is also meant to include that said fifth fraction is at least partially introduced into the second process.

When referred herein to a stream, a product or other composition, "rich in" a specific component, this generally means that this component is the major component, and in particular that the component is present in a concentration of more than 50 wt. %.

In accordance with the invention all or part of the third fraction rich in RSP, respectively all or part of the fourth fraction rich in RSP is introduced into a second process. Said third fraction, respectively said fourth fraction, may be directly introduced continuously or discontinuously into the second process. In at least a number of embodiments, it is sufficient to introduce 0.01 wt. % or more of said third fraction respectively said fourth fraction into a second process, in order to reduce energy consumption and/or increase production capacity in the first process for the production of cyclohexanone from phenol. In particular, at least 0.02 wt. %, at least 0.05 wt. %, at least 0.1 wt. %, at least 0.2 wt. %, or at least 0.5 wt. % of said third fraction respectively said fourth fraction may be introduced into a second process. In particular for a large reduction in energy consumption and/or a large increase in production capacity, preferably at least 1 wt. %, at least 2 wt. % or at least 5 wt. % of said third fraction respectively said fourth fraction is introduced into a second process. Up to 100 wt. % of the third, respectively the fourth fraction may be introduced into the second process. More preferably, 10-100 wt. %, or 25-100 wt. %, even more preferably 50-100 wt. % of said third fraction respectively said fourth fraction is introduced into a second process.

In an embodiment, the second process is a cyclohexane oxidation process, in which cyclohexanone and/or cyclohexanol is produced from cyclohexane. In an embodiment, the second process is a cyclohexanol dehydrogenation process, comprising use of a cyclohexanol dehydrogenation section in which cyclohexanol is at least partially converted into cyclohexanone, wherein thereafter in the second process cyclohexanone is separated from residual cyclohexanol and said further side-product from the first process.

In an embodiment, the second process is an adipic acid production process, wherein cyclohexanone and/or cyclohexanol is converted into adipic acid. It is to be noted that U.S. Pat. No. 4,306,944 discloses a process for hydrogenation of phenol to cyclohexanone, and shows (in FIG. 1) a reference to a prior art process in which stream "20" is not recycled because this would lead to an immediate extreme build-up of cyclohexanol in the system, but will be fed completely into an adipic acid production process. The invention of U.S. Pat. No. 4,306,944 is, however, aimed at introduction of a side-stream removal of a mixture of cyclohexanol and cyclohexanone in the first distillation column. U.S. Pat. No. 4,306,944 does not teach or suggest any problems regarding RSP or a solution of such problems.

In an embodiment, the second process is a process for preparing a phenol-formaldehyde resin.

The invention further relates to a chemical plant suitable for carrying out a method according to the invention, the plant comprising at least one cyclohexanone production installation and at least one further plant other than either said cyclohexanone production installation or a production installation for adipic acid, wherein the cyclohexanone production installation comprises a phenol hydrogenation reaction section (1);
downstream of the phenol hydrogenation reaction section (1), a plurality of distillation sections, at least sections (3), (4), and optionally (5), for separating the product stream of the phenol hydrogenation reaction section (1) into a first fraction and a second fraction, and said second fraction into a third and a fourth fraction;
an outlet (d and/or d2, h and/or h2, g and/or g2 e.g. as shown in FIGS. 2A, 2B, 3A, 3B and 4) from the cyclohexanone production installation to a further installation for preparing a chemical substance, wherein said outlet is arranged to introduce at least part of said third or said fourth fraction, into the different installation.

As mentioned above, the fourth fraction is usually at least partially subjected to a further fractionation by distillation, whereby a light fraction (the fifth fraction) comprising phenol and RSP is formed, which—according to an embodiment of the invention—is thereafter at least partially introduced into the second process. The small sixth fraction, enriched in heavies, is usually drained. Again, it is to be understood that the phrase "at least part of said fourth fraction" is also meant to include that said fifth fraction is at least partially introduced into the second process.

Preferably the plant comprises a recycling loop (comprising conduit d and/or d1, dehydrogenation section (6), and conduit h and/or h1) for converting at least part of the cyclohexanol in said third fraction from distillation section (4) into cyclohexanone, and feeding the resulting stream into distillation section (2). Moreover, the plant usually comprises a recycling loop (comprising conduit g) for recycling at least part of the aforementioned fifth fraction into hydrogenation section (1).

Preferably the plant comprises a recycling loop for recycling a part of said fourth fraction comprising phenol (conduit g and/or g1 as, for instance, shown in FIGS. 3A, 3B and 4) from the distillation section (5) to the phenol hydrogenation section (1) or distillation section (2). Moreover, the plant usually comprises a recycling loop (comprising conduit d, dehydrogenation section (6), and conduit h) for recycling at least part of the third fraction into distillation section (2).

Preferably, the further installation is selected from cyclohexane oxidation production installations, cyclohexanol dehydrogenation installations, and phenol-formaldehyde resin production installations.

As will be understood by the skilled person, the embodiments illustrated as examples in FIGS. 2 through 6, discussed herein below in more detail, or parts thereof may be combined to provide alternative embodiments of the invention. It is to be noted that in all of these Figures feed streams to numbered sections are represented as separate streams, but it will be evident to the skilled man that streams fed into a section may be combined before entering the section, or may enter the section separately. E.g. streams fed into a section may be introduced into a distillation column of the section at different levels of the column.

The hydrogenation of phenol can in principle be carried out in any way, in a vapour phase or in a liquid phase, e.g. based on any technology described in or referred to in Kirk-Othmer Encyclopedia of Chemical Technology $3^{rd}$ Edition, Vol 7, 1979 p. 410-416; I. Dodgson et al. "A low Cost Phenol to Cyclohexanone Process", Chemistry & Industry, 18, Dec. 1989, p 830-833; GB 890,095; Hancil and Beranek Chem. Eng. Sci., 25, 1970, p. 1121-1126; or Sakai et al. Nippon Kagaku Kaishi, 5, 1972, 821-829; Musser (in Ullmans's, see above); U.S. Pat. No. 2,829,166 or U.S. Pat. No. 3,076,810. The hydrogenation reaction section may comprise an internal recycling stream for recycling part of the stream leaving a reactor wherein the hydrogenation takes place. Product stream leaving the hydrogenation reaction section generally comprises cyclohexanone, cyclohexanol, phenol and RSP, usually including dicyclohexyl.

The distillation steps can be accomplished in a manner known in the art. Suitable distillation conditions can routinely be determined by the skilled person, based on common general knowledge and optionally some routine testing. In particular the skilled person may consult the prior art cited herein.

As indicated above, the process of the invention comprises the synthesis of cyclohexanone and a number of distillation steps, inter alia to recover cyclohexanone.

In general, the first fraction is rich in cyclohexanone, and enriched in cyclohexanone compared to the product stream. Preferably, the first fraction comprises at least 99 wt. % cyclohexanone, more preferably at least 99.8 wt. % cyclohexanone.

Said second fraction comprises at least one compound selected from cyclohexanol and phenol, usually both, and further RSP, in particular dicyclohexyl. In general, the second fraction is enriched in one or more of these compounds, compared to the product stream, whereas the second fraction has a lower cyclohexanone concentration than the product stream.

Figure 2A:
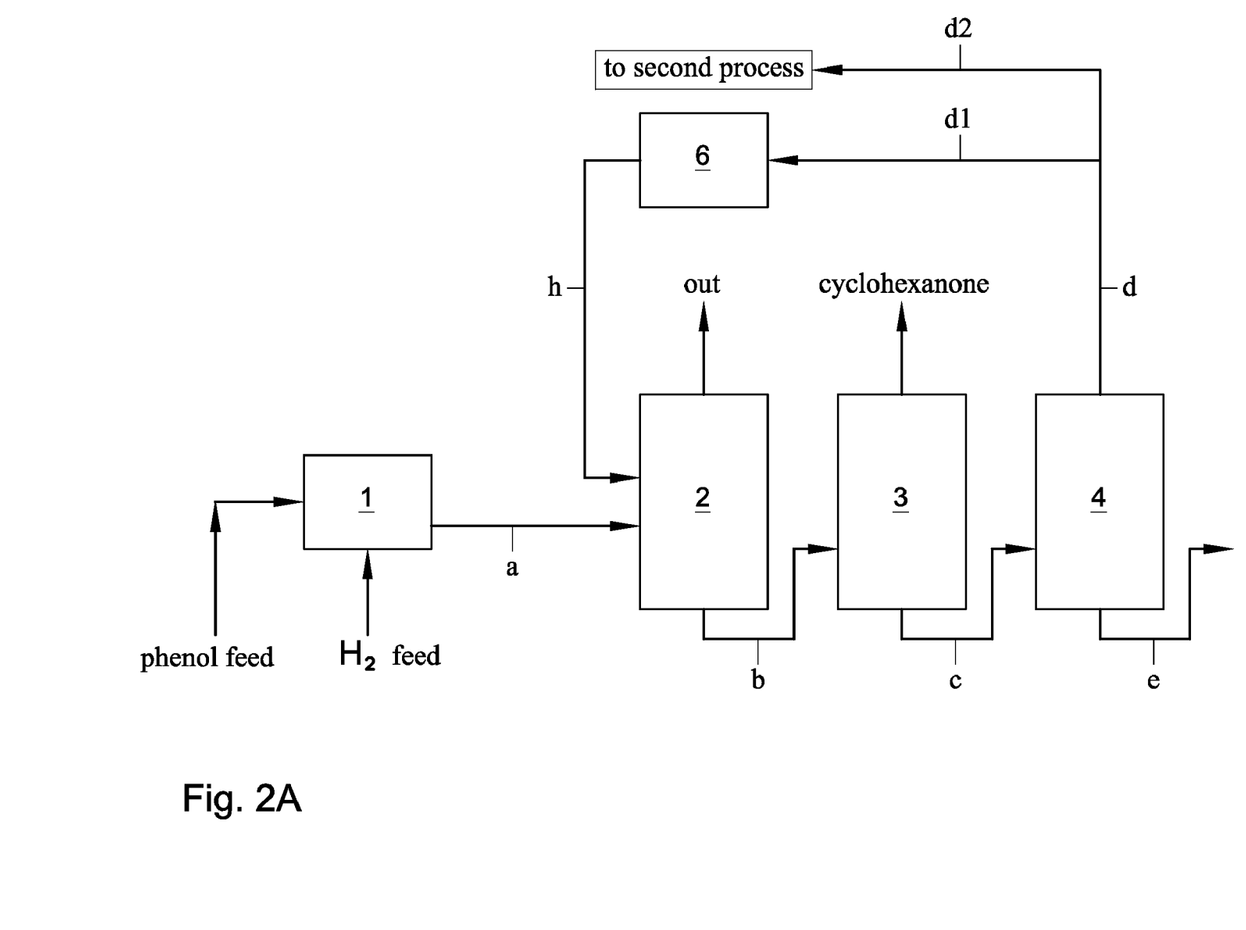
FIGS. 2A and 3A schematically show installations for carrying out a first process of a method of the invention, wherein at least part of a fraction rich in cyclohexanol is led to a second process.
Figure 2B:
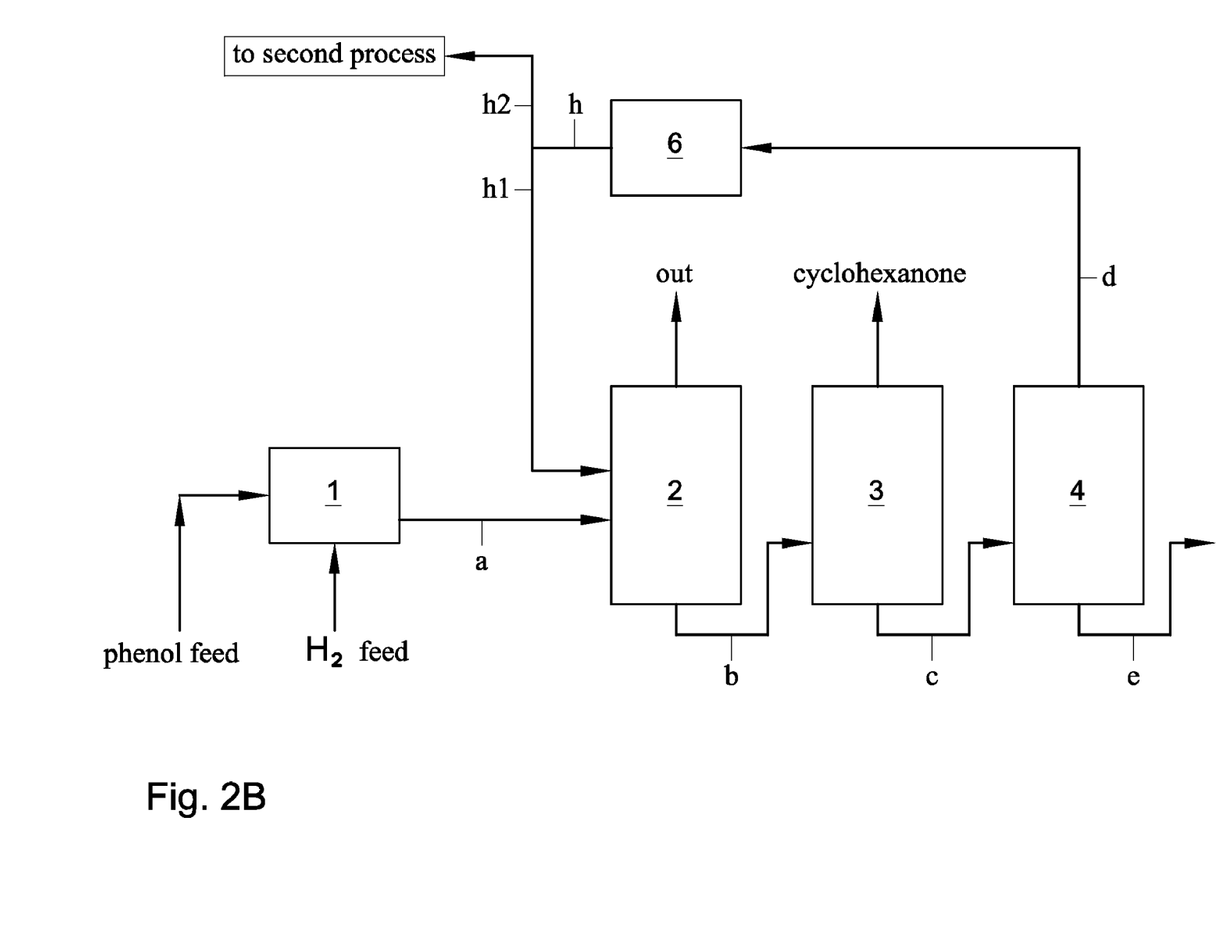
FIGS. 2B and 3B schematically show installations for carrying out a first process of a method of the invention wherein the fraction enriched in cyclohexanol is introduced in a dehydrogenation section, and at least part of the flow leaving that dehydrogenation section is led to a second process.

FIGS. 2A and 2B schematically show a cyclohexanone production installation for carrying out the first process in a method according to the invention. A phenol hydrogenation reaction section (1) is provided with an inlet for phenol and an inlet for hydrogen (which may be the same or different) and an outlet a for the product stream (comprising cyclohexanone, at least one useful compound selected from phenol and cyclohexanol (usually both), and RSP, such as dicyclohexyl, to lead the product stream to one or more distillation sections (2), (3), (4).

Outlet a can be directly connected to a distillation section (3), for recovering cyclohexanone, or to an optional pre-distillation section (2). Pre-distillation section (2) may be present to remove one or more compounds with a boiling point lower than cyclohexanone. This may be advantageous to improve recovery of the cyclohexanone.

If a pre-distillation section (2) is present, a conduit b is arranged to connect an outlet for a fraction comprising (usually enriched in) cyclohexanone—further comprising phenol and/or cyclohexanol, plus RSP—from pre-distillation section (2) to a main distillation section (3), for separating cyclohexanone from the other said compounds.

Conduit b is typically arranged to lead a heavy fraction (taken at or near the bottom of a distillation unit of the section) to the main distillation section (3). The main distillation section (3) serves to recover cyclohexanone. Herein cyclohexanone can be recovered as a light fraction, whereas phenol and/or cyclohexanol, plus RSP, in particular dicyclohexyl, predominantly form a heavy fraction. Conduit c may in principle be arranged to lead the latter fraction directly into the second process (which will be discussed in more detail below). As the latter fraction usually comprises both cyclohexanol and phenol, it is preferred to carry out a post-distillation, wherein cyclohexanol and phenol are separated from each other, although in principle both may be fed to the same further process, if this is not unacceptably detrimental to the performance of the further process.

In a preferred embodiment, a first post-distillation section (4) is provided to separate the feed entering section (4) via conduit c (heavy fraction from distillation section (3)) into a fraction enriched in cyclohexanol and a fraction enriched in phenol. Herein a light fraction enriched in cyclohexanol (for which conduit d provides an outlet) and a heavy fraction enriched in phenol (for which conduit e provides an outlet) can be formed. RSP may be predominantly in the fraction enriched in cyclohexanol, predominantly in the fraction enriched in phenol, or be distributed about equally over both fractions. Either of these fractions (or part thereof) may be led into a second process, provided that that fraction contains RSP, such as dicyclohexyl. It is also possible to lead one fraction (or part thereof) to a second process and the other (or part thereof) to a third process for preparing a substance of interest.

Preferably, distillation section (4) is provided with a conduit d for leading at least part of the fraction enriched in cyclohexanol—said fraction further comprising an RSP, such as dicyclohexyl—to a second process. Conduit e may be an outlet out of the installation or be arranged to lead the residue of section (4) to a further post-distillation section (5), see below.

Optionally, the (first) cyclohexanone production installation is provided with a loop to recycle a part of the third fraction (leaving section (4) via conduit d) to section (1), (2), or (3). FIGS. 2A and 2B show two preferred embodiments. In FIG. 2A conduit d is optionally divided into conduits d1 and d2, of which d2 is arranged to allow the third fraction or part thereof to be introduced in the second installation, and of which d1 is usually arranged to lead a part of fraction 4 into a dehydrogenation section (6) for partially converting cyclohexanol into cyclohexanone. In this embodiment conduit h is arranged to lead at least part of the stream leaving the dehydrogenation section (6) into any of the distillation sections, preferably section (2), if present, or section (3).

In FIG. 2B conduit d, which may be divided into a conduit d1 and d2, as in the embodiment illustrated by FIG. 2A, is arranged to lead a light fraction from distillation section (4) to dehydrogenation section (6). Herein, the dehydrogenation section is provided with a conduit h for the stream leaving dehydrogenation section (6). The conduit h is divided into conduits h1 and h2. Herein h1 is arranged as described for conduit h in FIG. 2A and h2 is arranged to allow the stream leaving dehydrogenation section (6) or part thereof to be introduced into the second installation.

Figure 3A:
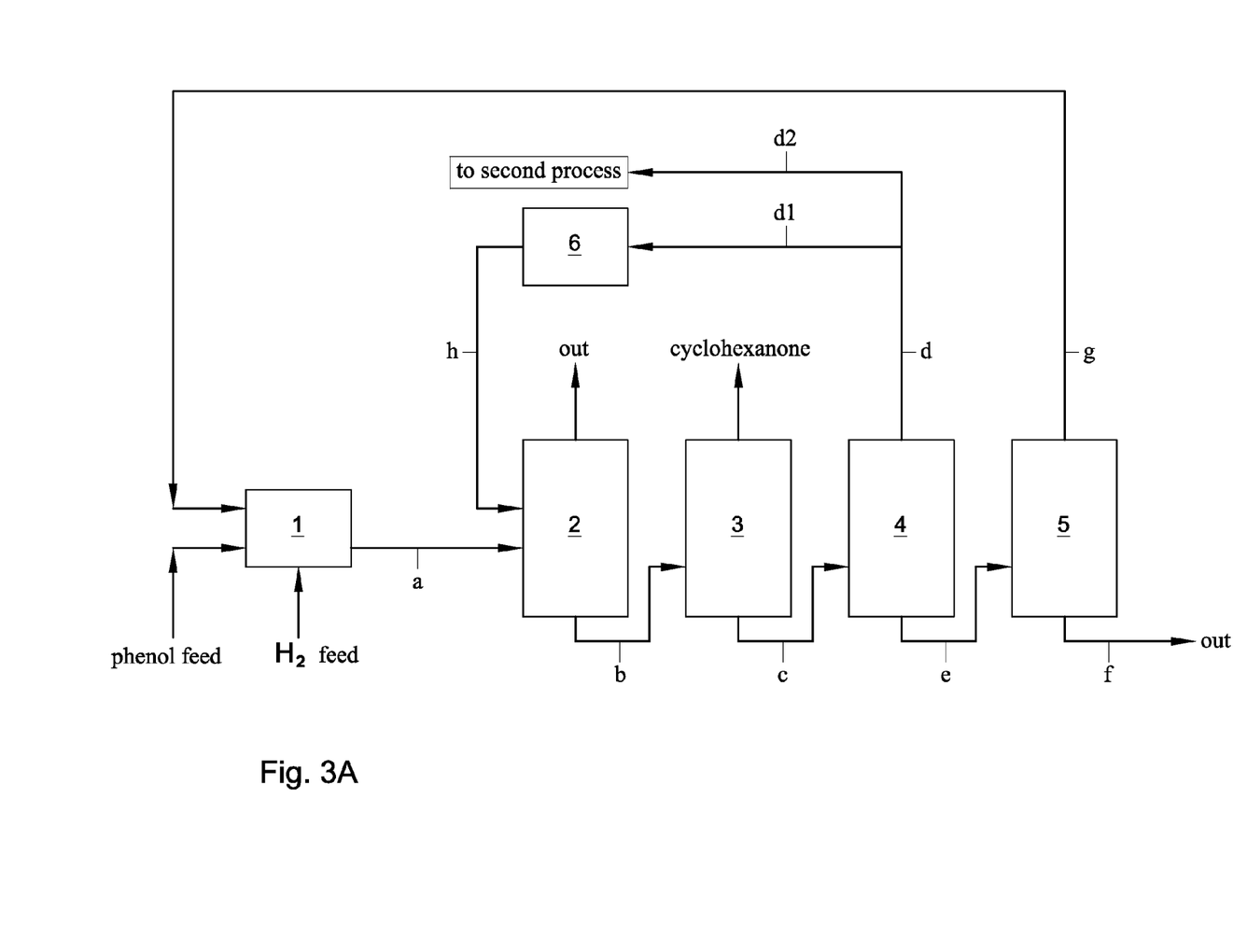
Figure 3B:
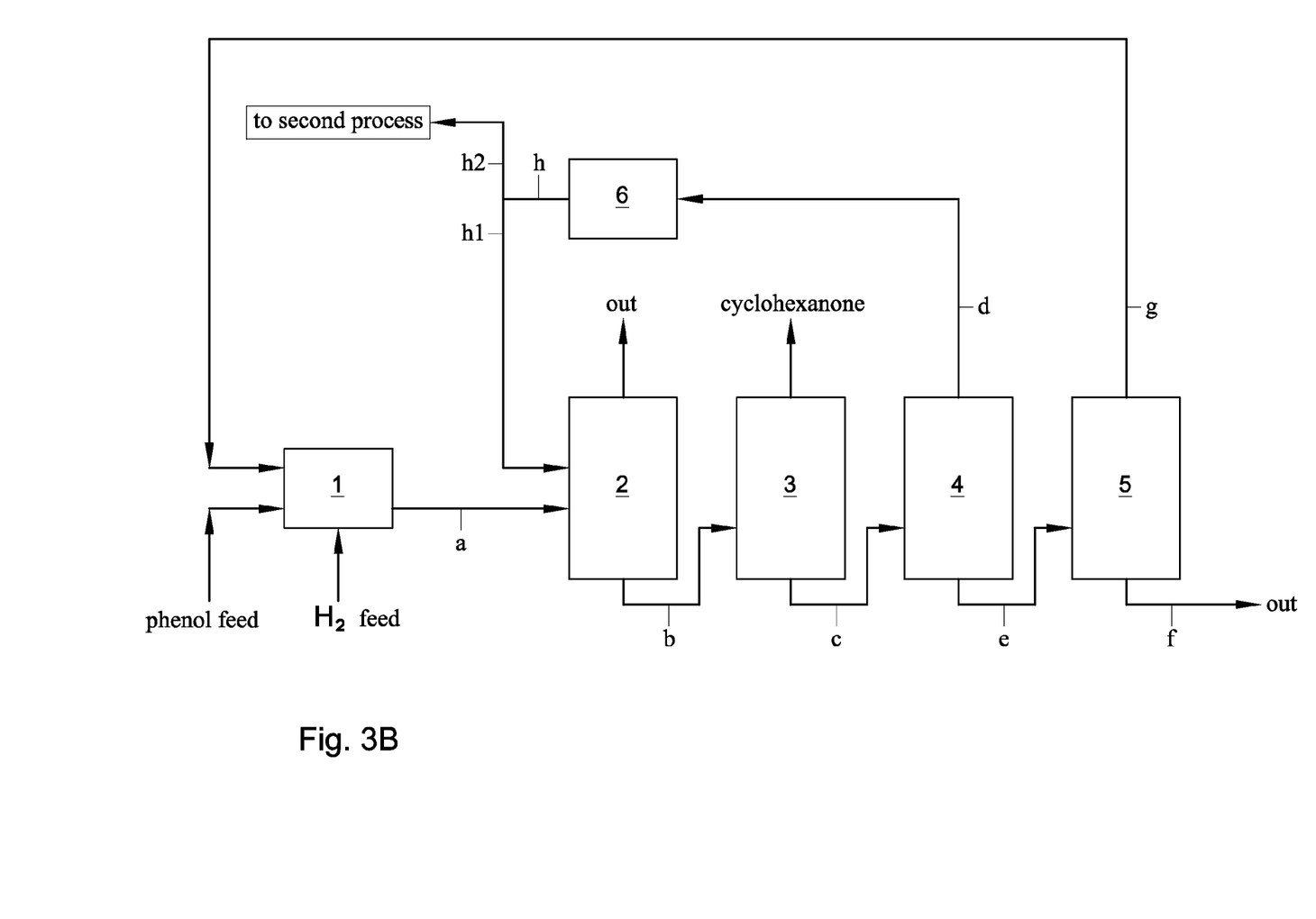

Particularly preferred installations for carrying out a method wherein cyclohexanol is led into a second process, are shown in FIGS. 3A and 3B. Items 1, 2, 3, 4, 6 and conduits a, b, c, d, e, h (including d1, d2, h1, h2) are as described for FIGS. 2A and 2B. Conduit d or—if present—d2 is for leading said fraction enriched in cyclohexanol—said fraction further comprising RSP, such as dicyclohexyl—or part thereof into the installation for a second process. In FIGS. 3A and 3B, a second post-distillation section (5) is provided to recover phenol. Conduit e is provided to lead the fraction enriched in phenol from post-distillation section (4) to a post-distillation section (5), for obtaining a fraction that is further enriched in phenol (compared to the feed to section (5)), typically a light fraction. In an installation according to FIG. 3B, the stream leaving dehydrogenation section (6) or part thereof is led to the second process via conduit h2.

Preferably, in a further embodiment of the invention conduit g is provided to recycle at least part of the fraction that is further enriched (and which may still comprise part of the undesired RSP) to the phenol hydrogenation reactor, for conversion into cyclohexanone.

Figure 4:
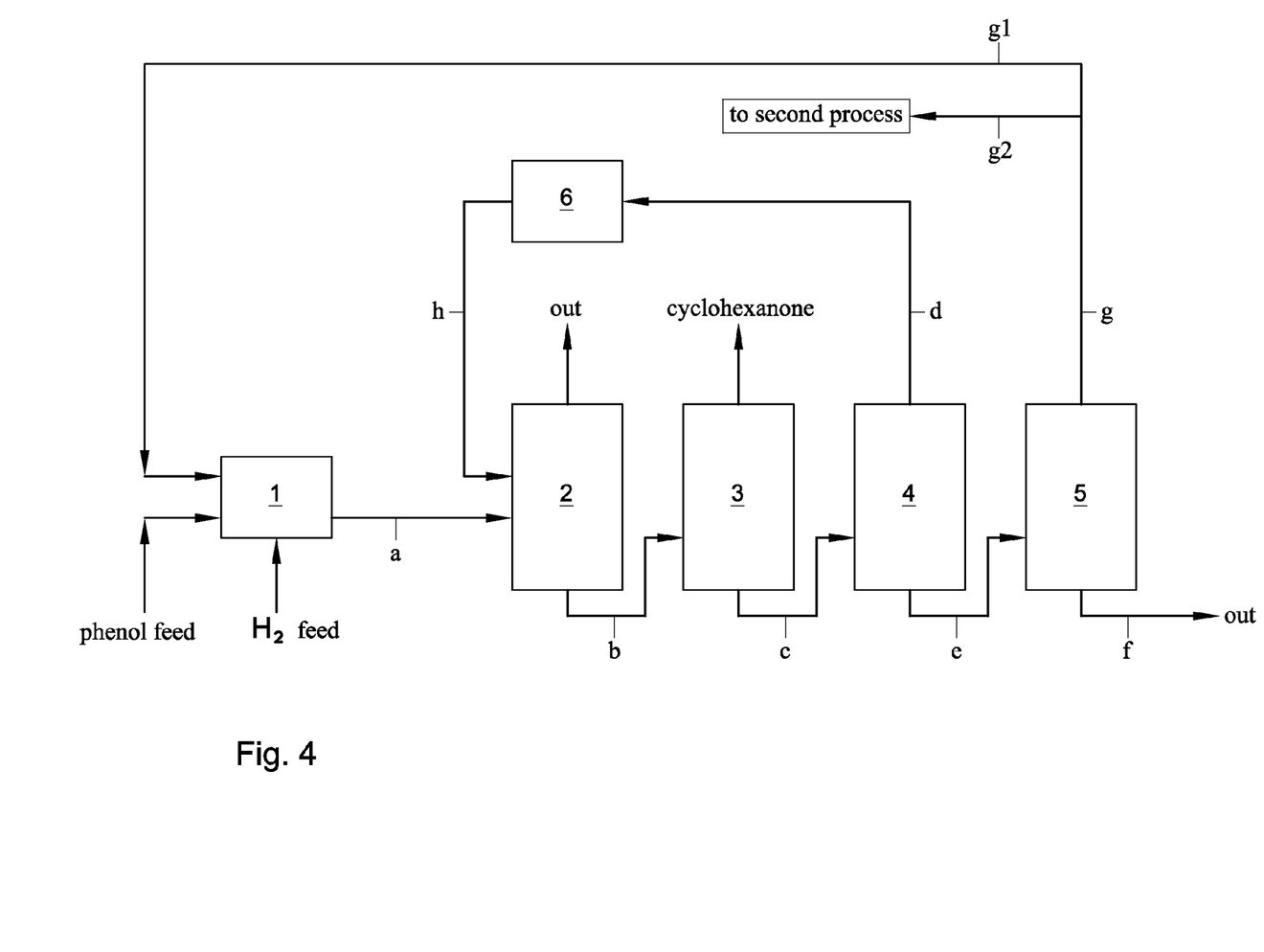
FIG. 4 schematically shows an installation for carrying out a first process of a method of the invention, wherein at least part of a fraction rich in phenol is led to a second process.

It is also possible to arrange conduit g to lead the phenol rich fraction from post distillation section (5), or part thereof, into a second process. FIG. 4 shows an embodiment, wherein conduit g is divided into at least two conduits (g1, g2), wherein at least one (g1) is for recycling phenol to section 1 and at least one (g2) is for feeding phenol into a second installation (not shown).

Thus, it is also possible to provide for the removal of RSP, by choosing separation conditions such that undesirable side-product is present in a fraction enriched in phenol. This fraction can be led to a different process to prepare a substance of interest from phenol, for instance a phenol resin.

Post-distillation section 5 further comprises an outlet for a remaining fraction (typically a heavy fraction). Usually, this fraction may be further processed, e.g. used for preparing a product like tar, asphalt, bitumen, shoe polish etc., incinerated or otherwise discarded.

In case undesirable side-product, in particular an RSP such as dicyclohexyl, is removed from the system via conduit g (or g2), and led into a different production process, conduit d may be arranged to feed the fraction enriched in cyclohexanol from distillation section (4) to a cyclohexanol dehydrogenation section (6), for partially converting cyclohexanol into cyclohexanone. Dehydrogenation section (6) may be provided with a conduit h, which may be arranged to lead the stream leaving dehydrogenation section (6) to distillation section (3), or distillation section (2) (if present). Optionally, conduit d or conduit h is divided such that a part of the stream leaving section (4) may be led into a second installation for a second process (cf. FIGS. 2A and 2B). The second installation may be the same or different as the installation to which an outlet of conduit g (or g2) is provided.

As indicated above, in a method according to the invention at least one fraction comprising a useful substance (cyclohexanol and/or phenol) and RSP, such as dicyclohexyl, is introduced into a second process, and optionally into a further process.

As the second or further process, respectively second or further installation, in accordance with the invention, in principle any process, respectively installation, can be used wherein RSP is (respectively can be) removed from the compound of interest produced in that process (respectively that can be produced in that installation). In particular, any such process respectively installation can be used wherein cyclohexanol or phenol is a suitable reagent for producing the substance of interest, wherein cyclohexanol or phenol is a suitable solvent or wherein cyclohexanol or phenol is the substance of interest. The second process, respectively installation, may thus be a process, respectively installation, for producing another substance of interest, or it may be a process, respectively installation, wherein cyclohexanone is produced (respectively can be) in a different way, in particular from a different starting compound, e.g. from cyclohexane.

It is contemplated that thus accumulation of an undesirable side-product, in particular dicyclohexyl, can substantially be avoided or at least considerably reduced. Thus, draining of a process stream fraction comprising not only RSP but also relatively valuable compounds can be avoided or at least reduced, whilst maintaining a desirably low energy consumption and/or a desirably high production capacity.

It is in particular contemplated that, even if initially some accumulation of any such undesirable side-product would occur, still a steady state situation will be reached wherein the rate of formation of such undesirable side-product and the rate of removal thereof will become equal, such that the steady state concentration of such undesirable side-product will be substantially lower than in a conventional process such as described above. In general, the steady state concentration is sufficiently low to reduce energy consumption and/or improve cyclohexanone production capacity, compared to a conventional process as shown in FIG. 1. In particular, a process according to the invention may be carried out without substantial disturbance of the process efficiency caused by RSP, such as dicyclohexyl. Thus, draining in order to remove RSP is no longer needed, or at least the periods between to draining operations can be increased considerably. Without being bound by theory, it is envisaged that the steady state concentration of RSP, in particular of dicyclohexyl, may be at least 10 times lower, preferably at least 50 times lower or even at least 100 times lower than in a comparable process.

In an embodiment, the fraction comprising cyclohexanol and RSP—such as dicyclohexyl—originating from the cyclohexanone production plant (for preparing cyclohexanone from phenol) may be introduced into cyclohexane oxidation plant (as an example of a second installation), wherein cyclohexanol and/or cyclohexanone are produced. The fraction may in principle be fed into any part of the cyclohexane oxidation plant, for instance into a cyclohexane oxidation reactor, into a cyclohexane distillation section, into a dehydrogenation section, or into a purification section, in which the reaction product stream may be separated into a fraction rich in cyclohexanone and/or cyclohexanol and a fraction comprising (most of the) RSP. In the purification section, usually a distillation section, cyclohexanone/cyclohexanol is recovered (as the light fraction, if distillation is used; in case both are to be recovered in separate fractions, usually at least two distillation columns are used). RSP from the first cyclohexanone production process, (predominantly) resides in the remaining fraction (a heavy fraction, if distillation is used).

The cyclohexane oxidation process (installation) may for instance be based on a process (installation) as described or referred to in Musser (in Ullman's Encyclopedia, see above), of which the contents, in particular FIGS. 2 and 3 and the description thereof, are incorporated by reference.

In an embodiment, the second process is a process for the preparation of adipic acid. Adipic acid is a useful reagent, inter alia for the production of polymers such as polyamides (nylon 6,6). In the adipic acid plant a mixture of cyclohexanol and cyclohexanone is converted into adipic acid. Suitable conversion processes are generally known in the art and include for instance a reaction with nitric acid and/or oxygen. The adipic acid can be separated from undesirable side-product (such as dicyclohexyl), e.g. by crystallisation, extraction or distillation, or be converted in the process. This process may for instance be based on a process as described in Ullmanns Encyklopädie der technischen Chemie, 4$^{th}$ Edition, Volume 7, p. 106-109, of which the contents are incorporated herein by reference, in particular with respect to FIG. 1 and the description thereof, or in Kirk-Othmer, Encyclopedia of Chemical Technology, third edition, Volume 1, p. 510-523.

Figure 5:
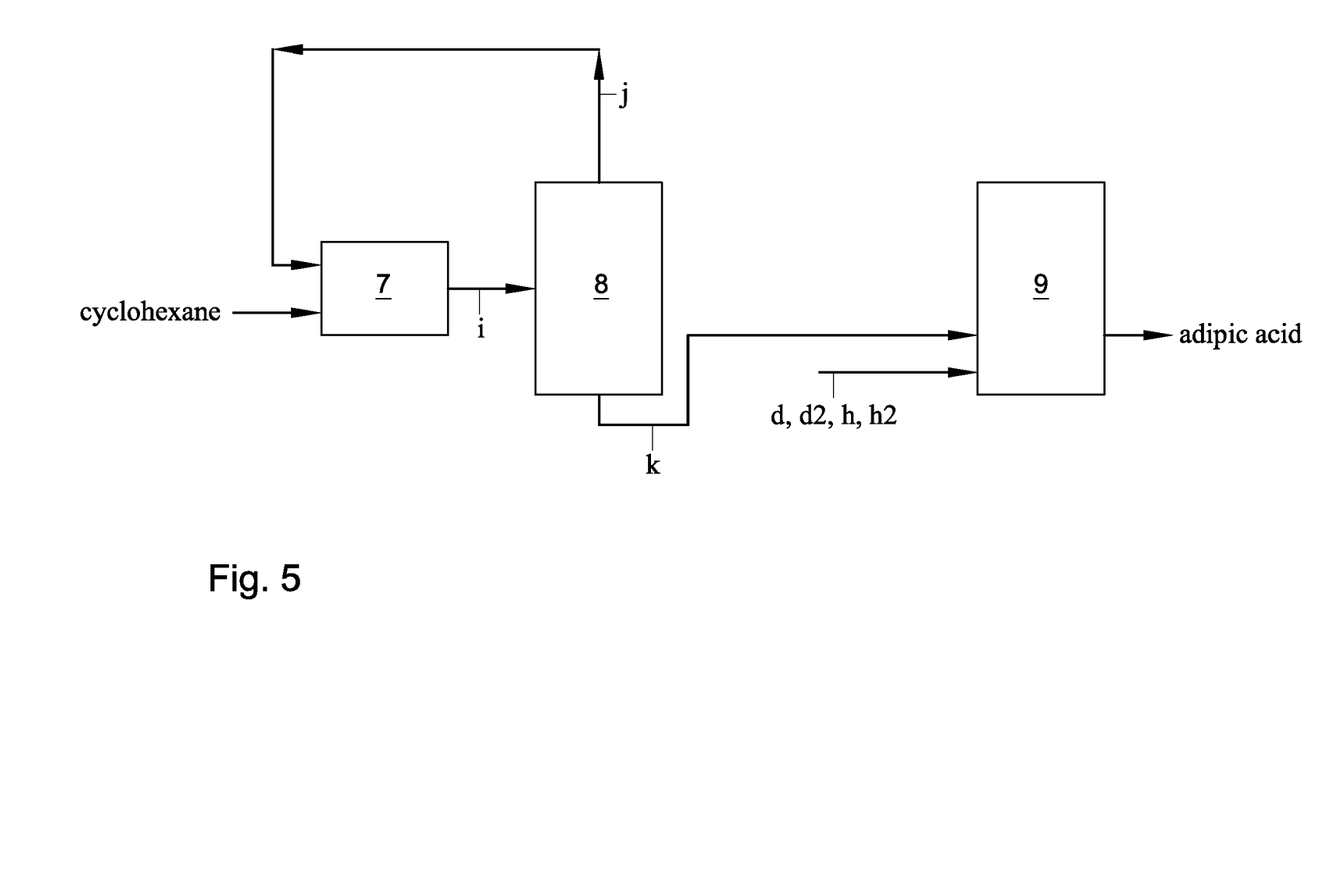
FIGS. 5 and 6 schematically show (detailed parts of) installations for carrying out specific embodiments of a second process of a method of the invention, respectively a cyclohexane oxidation process leading to adipic acid (FIG. 5) and a cyclohexanone production installation based on cyclohexane feedstock (FIG. 6).

FIG. 5 schematically shows a particularly suitable design for an adipic acid production installation wherein cyclohexane is oxidized into a mixture containing cyclohexanol and cyclohexanone. This installation comprises a reaction section (7) for oxidising cyclohexane. A conduit i is provided to lead the reaction product to a separation section (8) (such as a distillation section) wherein unreacted cyclohexane (light fraction) can be separated from cyclohexanol/cyclohexanone (and other heavies, in case section (8) is a distillation section) which may be present (heavy fraction). A recycle loop j is provided to recycle unreacted cyclohexane to reaction section (7). A conduit k is provided for leading the heavy fraction to the adipic acid production section (9). Conduit d, d2, h, or h2 from the first process may also be arranged to introduce the contents thereof into section (9). RSP can be led into the second process without causing unacceptable problems.

In an embodiment (illustrated in FIG. 6), the third fraction, rich in cyclohexanol and comprising RSP (such as dicyclohexyl), is introduced (via conduit d, d2, h or h2) into the cyclohexanol dehydrogenation part of a cyclohexanone production plant based on cyclohexane feedstock, comprising dehydrogenation section (10), in which cyclohexanol is partially converted into cyclohexanone. The dehydrogenation section (10) is provided with a conduit l for leading the stream leaving the dehydrogenation section to a separation section (11), wherein a crude mixture of cyclohexanol and cyclohexanone from the cyclohexane oxidation section of the cyclohexanone production plant (based on cyclohexane feedstock) is purified for production of pure cyclohexanone. Optionally, a pre-distillation section is arranged between dehydrogenation section (10) and separation section (11) (not shown). With the pre-distillation section, lights can be removed (compare section (2) in FIGS. 1 through 4).

Figure 6:
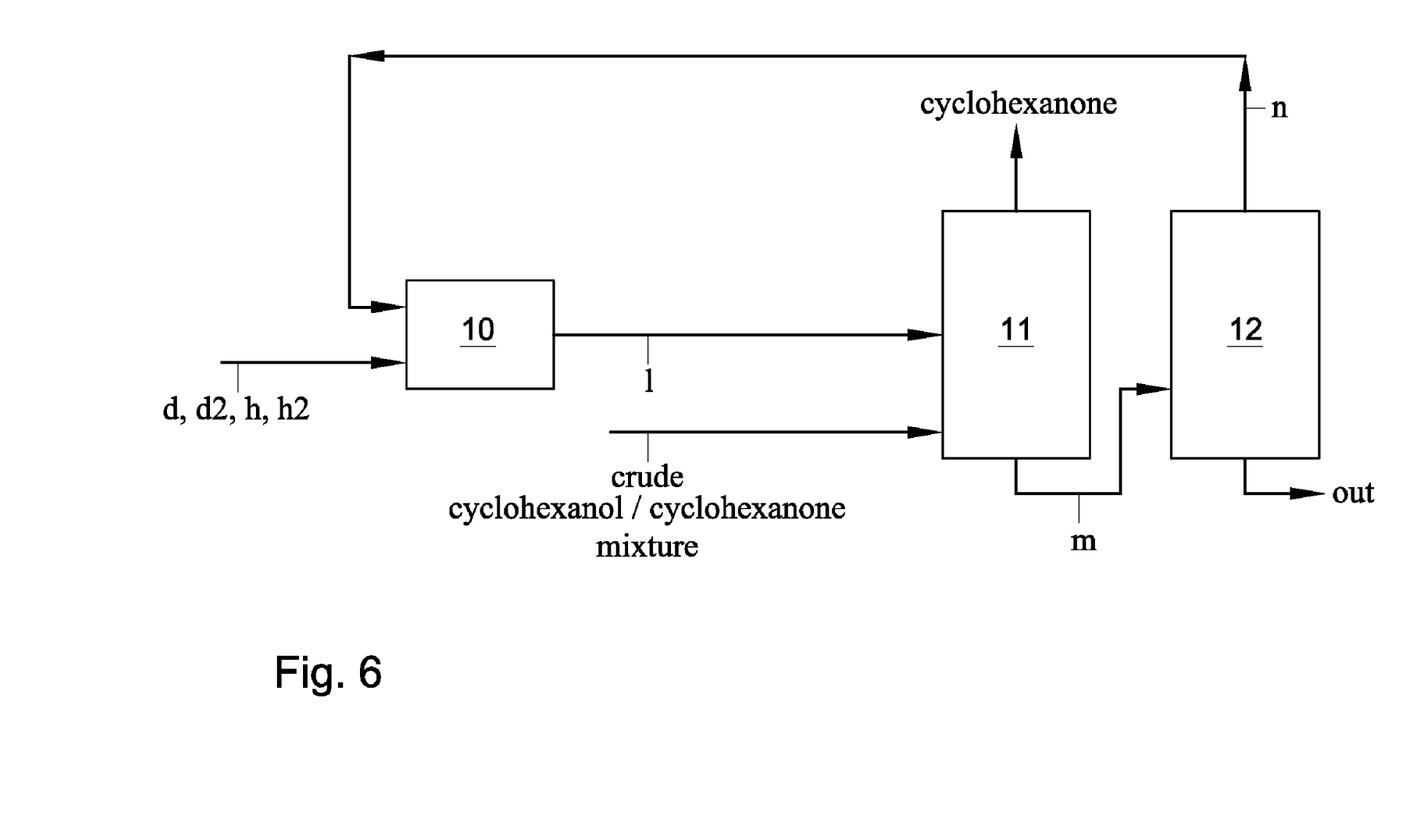

The separation section (11) preferably comprises a distillation section for recovering cyclohexanone as a light fraction and residual cyclohexanol plus RSP in a heavy fraction. A conduit m is provided to lead residual cyclohexanol and RSP to post-separation section (12). This section (12) serves to effectively separate cyclohexanol from RSP, in particular dicyclohexyl. Preferably, a conduit n is arranged to recycle cyclohexanol to dehydrogenation section (10). Post-separation section (12) preferably comprises a post-distillation section for separating cyclohexanol as a light fraction from RSP, such as dicyclohexyl, in a heavy fraction.

In an embodiment, wherein the second fraction comprises phenol and RSP (such as dicyclohexyl), the second process (into which the second fraction is introduced) may in particular be a process for preparing a phenol-formaldehyde resin. Such process may, e.g., be based on a process as described in Kirk-Othmer Encyclopedia of Chemical Technology, third Edition, Volume 17, p. 390-399.

The invention is now illustrated by the following examples.

EXAMPLES

General Set-Up

The comparative example is based on an installation as schematically shown in FIG. 1 is. The examples according to the invention are based on an installation as schematically shown in FIGS. 3A and 4 (as indicated). The reaction section (1) comprises a gas-phase phenol hydrogenation reactor, containing a palladium hydrogenation catalyst (1% Pd on carbon, Na-doped). Dehydrogenation section (6) comprises a gas phase cyclohexanol converter. The distillation is conventional.

The following main flows are identified as follows:

Feed of hydrogen gas and feed of phenol are introduced in the reaction section (1).

The product flow leaving reaction section (1) contains cyclohexanone, cyclohexanol, phenol and by-products, including RSP, in particular dicyclohexyl. The bottom flow b of distillation section (2) contains cyclohexanone, cyclohexanol, phenol and by-products, including RSP, in particular dicyclohexyl.

The top flow ('out') of distillation section (2) contains light compounds, such as benzene, cyclohexane and water.

The bottom flow c of distillation section (3) contains cyclohexanone, cyclohexanol, phenol and by-products, including RSP, in particular dicyclohexyl.

The top flow of section (3) contains purified cyclohexanone.

The bottom flow of section (4) (through conduit e) contains cyclohexanone, cyclohexanol, phenol and by-products, including RSP, in particular dicyclohexyl.

In the comparative experiment, the top flow of distillation section (4), is fed to dehydrogenation section (6) via conduit d. This flow contains amongst others cyclohexanol, cyclohexanone and by-products. In dehydrogenation section (6) cyclohexanol is converted to cyclohexanone. The stream h contains cyclohexanone, cyclohexanol, and by-products, including RSP, in particular dicyclohexyl.

In the process of the invention (the results of which are obtained herein by mathematical simulation), the top flow of section (4) in FIG. 3A leaves the installation (to a different installation for the second process) via conduits d and d2.

The bottom flow of distillation section (5) (via conduit f) contains phenol, cyclohexanone, cyclohexanol, and by-products (hardly any RSP).

The top flow of section (5), which is fed to reaction section (1) via conduit g, contains amongst others phenol, cyclohexanone, cyclohexanol and by-products including RSP, in particular dicyclohexyl. In the process of the invention, the top flow of section (5) in FIG. 4 leaves the installation (to a different installation for the second process) via conduits g and g2.

Comparative Example

The steady state situation was simulated based on a mass balance obtained in a conventional cyclohexanone production plant based on a phenol feedstock.

This installation runs at an average cyclohexanone production capacity of 34 000 kg/hr. The whole top flow of distillation section 4 is sent to a cyclohexanol dehydrogenation section (6) (FIG. 1).

The formation rate of dicyclohexyl in this plant is approx. 0.20 kg per hour. Dicyclohexyl could not be detected in any of the phenol feed flow, the hydrogen feed flow, the cyclohexanone flow leaving distillation section (3), or the lights flow leaving distillation section (2) of the cyclohexanone production plant.

The ratio of the amount of dicyclohexyl leaving via stream d section (4) to the amount of dicyclohexyl in the feed to section (4) (stream c) is 0.167 to 0.333

At a certain moment the feed flow to section (4) (flow c) was 5500 kg/hr, of which about 250 kg/hr was dicyclohexyl.

At the same moment the rate at which dicyclohexyl was removed from this plant via stream f was 0.023 kg/h. So, the ratio of the amount of dicyclohexyl in the heavy fraction leaving section (5) (stream f) to the amount of dicyclohexyl in the feed to section (4) (stream c) of approximately 0.0001, i.e. essentially all dicyclohexyl is recycling in the plant, as shown in FIG. 1.

The ratio of the amount of dicyclohexyl in the light fraction of section (5) (stream g) to dicyclohexyl in the feed c to section (4) is 0.833 to 0.667.

Under conventional continuous plant operation without additional draining, as described in the introduction part of this specification, the amount of dicyclohexyl in the feed to section (4) (stream c) continuously increases and therefore the removal rate of dicyclohexyl in the bottom fraction of section (5) continuously increases (stream f) until the removal rate of dicyclohexyl is equal to the production rate of dicyclohexyl. Under steady state conditions for the flow rate of dicyclohexyl in the feed to section (4) (flow c) is approximately 2000 kg/hr. So, under these steady state conditions the total feed to section (4) (stream c) amounts to 7250 kg/hr, with a dicyclohexyl content of 27.6% by weight. It is estimated by simulation that under conventional continuous plant operation without additional draining, as described in the description above, when discussing FIG. 1, 90% of this steady state (flow of stream c is 7050 kg/hr of which 1800 kg/hr is dicyclohexyl) would be reached after a period of more than 2 years of operation after start-up of the plant. In practice this condition is never reached because at a lower content of dicyclohexyl section (4) already gets overloaded, energy consumption is increased and separation becomes worse.

Examples According to the Invention

The basic data, shown above, obtained from a mass balance of a conventional cyclohexanone production process based on a phenol feedstock was used, but now part or complete streams were sent to a second process according to the invention.

Example 1

In this example, the steady state dicyclohexyl flow is calculated in case the top stream d, from section (4) is fully introduced into a second process as schematically shown in FIG. 3A.

Outlets for dicyclohexyl out of the first process are the top stream d leaving section (4) and bottom stream f of section (5).

Steady state dicyclohexyl concentrations are reached when the sum of the dicyclohexyl flows in these outlets equals the production rate of dicyclohexyl.

The steady state flows depend on the ratio dicyclohexyl in stream d to dicyclohexyl in stream c, which is between 0.167 and 0.333.

In case the ratio is 0.167: the steady state flow of dicyclohexyl in stream c is 0.20/(0.167+0.0001)=1.20 kg/hr.

In case the ratio is 0.333: the steady state flow of dicyclohexyl in stream c is 0.20/(0.333+0.0001)=0.60 kg/hr.

So, under these conditions the steady state total feed c is between 5251.20 kg/hr (5250+1.20 kg/hr) and 5250.60 kg/hr (5250+0.60 kg/hr).

This feed contains maximally 1.20/(5250+1.20)=0.023 wt. % dicyclohexyl.

Accordingly, the steady state flow for dicyclohexyl building up in the process is drastically reduced.

Example 2

In this example, the maximum dicyclohexyl flow is calculated in case one third of the top stream d leaving from section (4) is introduced into a second process (i.e. stream d2) and two thirds (stream d1) are led to section (6) wherein at least part of the cyclohexanol is dehydrogenated and led back into section (2) (FIG. 3A).

Outlets for dicyclohexyl out of the first process are stream d2 (part of top stream leaving section (4)) and bottom stream f of section (5).

Steady state dicyclohexyl concentrations are reached when the sum of the dicyclohexyl flows in these outlets equals the production rate of dicyclohexyl.

The steady state flows depend on the ratio dicyclohexyl in stream d to dicyclohexyl in stream c, which is between 0.167 and 0.333.

In case the ratio is 0.167: the steady state flow of dicyclohexyl in stream c is 0.20/(0.333*0.167+0.0001)=3.59 kg/hr.

In case the ratio is 0.333: the steady state flow of dicyclohexyl in stream c is 0.20/(0.333*0.333+0.0001)=1.80 kg/hr.

So, under these conditions the maximum total steady state feed c is 5253.59 kg/hr (5250+3.59 kg/hr).

This feed contains maximally 3.59/(5250+3.59)=0.068 wt. % dicyclohexyl.

Accordingly, it is shown that it is sufficient to lead a minor fraction of the top stream from a first post distillation into a second process in order to reduce the steady state flows for dicyclohexyl building up in the process drastically.

Example 3

The effect of a further reduction of the fraction d2 of top stream d (FIG. 3A) that is introduced into a second process has been calculated analogously. In this example, the maximum dicyclohexyl flow is calculated in case as low as 2 wt. % of the top stream d leaving from section 4 is introduced into a second process (i.e. stream d2) and 98 wt. % (stream d1) are led to section (6) wherein at least part of the cyclohexanol is dehydrogenated and led back into section (2) (FIG. 3A).

Outlets for dicyclohexyl out of the first process are stream d2 (part of top stream leaving section (4)) and bottom stream f of section (5).

Steady state dicyclohexyl concentrations are reached when the sum of the dicyclohexyl flows in these outlets equals the production rate of dicyclohexyl.

The steady state flows depend on the ratio dicyclohexyl in stream d to dicyclohexyl in stream c, which is between 0.167 and 0.333.

In case the ratio is 0.167: the steady state flow of dicyclohexyl in stream c is 0.20/(0.02*0.167+0.0001)=58.25 kg/hr.

In case the ratio is 0.333: the steady state flow of dicyclohexyl in stream c is 0.20/(0.02*0.333+0.0001)=29.56 kg/hr.

So, under these conditions the maximum total steady state feed c is 5308.25 kg/hr (5250+58.25 kg/hr).

This feed contains maximally 58.25/(5250+58.25)=1.1 wt. % dicyclohexyl.

The calculation was repeated with situations wherein even a smaller fraction is led into a second process. This gave the following results:

| Fraction into $2^{nd}$ process (wt. %) | Max wt. % dicyclohexyl in feed c |
|---|---|
| 1 | 2.1 |
| 0.5 | 3.9 |
| 0.2 | 8.1 |
| 0.1 | 12.5 |
| 0.05 | 17.2 |

Accordingly, it is shown that even a very minor fraction of the top stream from a first post distillation into a second process reduces the steady state flows for dicyclohexyl building up in the process already significantly.

Example 4

In this example, the maximum dicyclohexyl flow is calculated in case 5 wt. % of the top stream g leaving from section (5) in FIG. 4 is introduced into a second process (i.e. stream g2) and 95 wt. % (stream g1) are led to section (1) wherein the phenol hydrogenation occurs (FIG. 4).

Outlets for dicyclohexyl out of the first process are stream g2 (part of top stream leaving section (5)) and bottom stream f of section (5).

Steady state dicyclohexyl concentrations are reached when the sum of the dicyclohexyl flows in these outlets equals the production rate of dicyclohexyl.

The steady state flows depend on the ratio dicyclohexyl in stream g to dicyclohexyl in stream c, which is between 0.667 and 0.833.

In case the ratio is 0.667: the steady state flow of dicyclohexyl in stream c is 0.20/(0.05*0.667+0.0001)=5.98 kg/hr.

In case the ratio is 0.833: the steady state flow of dicyclohexyl in stream c is 0.20/(0.05*0.833+0.0001)=4.79 kg/hr.

So, under these conditions the maximum total steady state feed c is 5255.98 kg/hr (5250+5.98 kg/hr).

This feed contains maximally 5.98/(5250+5.98)=0.11 wt. % dicyclohexyl. Accordingly, it is shown that a very small fraction of the top stream from a second post distillation into a second process is sufficient to reduce the steady state flows for dicyclohexyl building up in the process drastically significantly.

In a simulation wherein only 5 wt. % of stream g was introduced into a second process, the dicyclohexyl equilibrium concentration was calculated to be 0.11 wt. %, which is a considerable reduction.

All examples according to the invention shows significant reductions in the steady state flows of dicyclohexyl, which provides considerable benefits with respect to energy consumption and the like.

The calculation was repeated with situations wherein varying fractions are led into a second process. This gave the following results:

| Fraction into 2$^{nd}$ process (wt. %) | Max wt. % dicyclohexyl in feed c |
|---|---|
| 100 | 0.006 |
| 25 | 0.023 |
| 10 | 0.056 |
| 2 | 0.28 |
| 1 | 0.56 |
| 0.5 | 1.1 |
| 0.2 | 2.6 |
| 0.1 | 4.7 |
| 0.05 | 8.1 |
| 0.03 | 11.3 |
| 0.02 | 14.0 |
| 0.01 | 18.6 |

The examples show, that in accordance with the invention a stream containing dicyclohexyl can be led fully or partially into a second process. This can be chosen within wide limits, for instance 100 wt. % to 0.5 wt. % or even below 0.5 wt. % of such stream can be led into the second process.

The invention claimed is:

1. Method for preparing cyclohexanone from phenol in a first process, the first process being a cyclohexanone production process making use of a catalyst comprising at least one catalytically active metal selected from platinum and palladium, comprising
    a) hydrogenating phenol to form a product stream comprising cyclohexanone, phenol and side-products, including cyclohexanol and recycling side product (RSP);
    b) separating at least part of the product stream, or at least part of the product stream from which one or more components having a lower boiling point than cyclohexanone have been removed, into a first fraction comprising cyclohexanone and a second fraction comprising phenol, cyclohexanol and RSP, using distillation;
    c) separating the second fraction into a third fraction, rich in cyclohexanol and comprising RSP, and a fourth fraction, rich in phenol and usually comprising RSP, using distillation; and
    d) continuously or discontinuously introducing at least part of said third fraction rich in cyclohexanol and comprising RSP into a second process, in which second process RSP is removed from cyclohexanol and/or a conversion product of cyclohexanol formed in the second process.

2. Method for preparing cyclohexanone from phenol in a first process according to claim 1, wherein the introducing into a second process of at least part of said third fraction rich in cyclohexanol and comprising RSP in step d) is done after said at least part has been treated in a dehydrogenation process.

3. Method according to claim 1, wherein 0.5-100 wt. % of said third fraction is introduced into the second process.

4. Method according to claim 1, wherein the second process is a cyclohexane oxidation process, in which cyclohexanol and/or cyclohexanone is produced from cyclohexane.

5. Method according to claim 1, wherein the second process comprises a cyclohexanol dehydrogenation into cyclohexanone, and wherein in the second process cyclohexanone formed by said dehydrogenation is separated from residual cyclohexanol and RSP originating from the first process.

6. Method according to claim 1, wherein the second process is an adipic acid production process.

7. Method for preparing cyclohexanone from phenol in a first process, the first process being a cyclohexanone production process making use of a catalyst comprising at least one catalytically active metal selected from platinum and palladium, comprising
    a) hydrogenating phenol to form a product stream comprising cyclohexanone, phenol and side-products, including cyclohexanol and recycling side product (RSP);
    b) separating at least part of the product stream, or at least part of the product stream from which one or more components having a lower boiling point than cyclohexanone have been removed, into a first fraction comprising cyclohexanone and a second fraction comprising phenol, cyclohexanol and RSP, using distillation;
    c) separating the second fraction into a third fraction, rich in cyclohexanol and usually comprising RSP, and a fourth fraction, rich in phenol and comprising RSP, using distillation; and
    d) continuously or discontinuously introducing at least part of said fourth fraction rich in phenol and comprising RSP into a second process, in which second process RSP is removed from phenol and/or a conversion product of phenol formed in the second process.

8. Method according to claim 7, wherein 0.5-100 wt. % of said fourth fraction is introduced into the second process.

9. Method according to claim 7, wherein the second process is a process for preparing a phenol-formaldehyde resin.

10. Method according to claim 1, wherein the RSP comprises dicyclohexyl.

* * * * *